United States Patent [19]
Hutchinson

[11] Patent Number: 5,922,883
[45] Date of Patent: Jul. 13, 1999

[54] INHIBITORS OF FARNESYL-PROTEIN TRANSFERASE

[75] Inventor: John H. Hutchinson, Philadelphia, Pa.

[73] Assignee: Merck & Co., Inc., Rahway, N.J.

[21] Appl. No.: 08/824,427

[22] Filed: Mar. 26, 1997

Related U.S. Application Data

[60] Provisional application No. 60/014,776, Apr. 3, 1996.

[51] Int. Cl.$^6$ ...................... C07D 233/61; C07D 233/54; A61K 31/415
[52] U.S. Cl. ...................... 548/338.1; 514/398; 514/399; 548/338.5
[58] Field of Search .................. 548/338.1; 514/398, 514/399

[56] References Cited

U.S. PATENT DOCUMENTS

| | | | |
|---|---|---|---|
| 5,278,148 | 1/1994 | Branca et al. | 514/19 |
| 5,534,537 | 7/1996 | Ciccarone et al. | 514/397 |
| 5,571,792 | 11/1996 | Bolton et al. | 514/18 |
| 5,576,313 | 11/1996 | Fisher et al. | 514/211 |
| 5,756,528 | 5/1998 | Anthony et al. | 514/399 |

FOREIGN PATENT DOCUMENTS

| | | |
|---|---|---|
| 0 675 122 A1 | 10/1995 | European Pat. Off. . |
| WO 94/19326 | 9/1994 | WIPO . |
| WO 96/30343 | 10/1996 | WIPO . |
| WO 96/37204 | 11/1996 | WIPO . |

OTHER PUBLICATIONS

Exp. Opin. Ther. Patents, vol. 5(12) (1995), pp. 1269–1285, by S. L. Graham.
Exp. Opin. Ther. Patents, vol. 6(12) (1996), pp. 1295–1304, by S. L. Graham, et al.
J. of Biol. Chem., vol. 268, No. 11, pp. 7617–7620 (1993), by J. B. Gibbs, et al.
J. of Biol. Chem., vol. 269, No. 44, pp. 27706–27714 (1994), by G. L. James, et al. I.
J. of Biol. Chem., vol. 270, No. 11, pp. 6221–6226 (1995), by G. L. James, et al. II.
Science, vol. 260, pp. 1934–1937 (1993), by N. E. Kohl, et al. I.
Proc. Natl. Acad. Sci. USA, vol. 91, pp. 9141–9145 (1994), by N. E. Kohl, et al. II.
Nature Medicine, vol. 1, No. 8, pp. 792–797 (1995), by N. E. Kohl, et al. III.
Cancer Research, vol. 55, pp. 5302–5309 (1995), by L. Sepp–Lorenzino, et al.

*Primary Examiner*—Floyd D. Higel
*Attorney, Agent, or Firm*—Dianne Pecoraro; David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

28 Claims, No Drawings

INHIBITORS OF FARNESYL-PROTEIN TRANSFERASE

DOMESTIC PRIORITY CLAIM

This application claims the benefit of U.S. Provisional Application No. 60/014,776, filed on Apr. 3, 1996.

BACKGROUND OF THE INVENTION

The present invention relates to compounds which inhibit farnesyl protein transferase, a protein which is implicated in the oncogenic pathway mediated by Ras. The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). Ras proteins are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific, and thus preferable.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)).

It has recently been reported that FPT-ase inhibitors also inhibit the proliferation of vascular smooth muscle cells and are therefore useful in the prevention and treatment of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

SUMMARY OF THE INVENTION

The present invention addresses a compound of formula I:

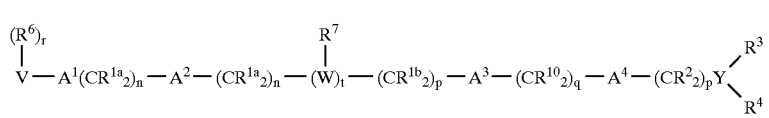

I or a pharmaceutically acceptable salt thereof, wherein:

$R^{1a}$, $R^{1b}$, $R^2$ and $R^{10}$ are independently selected from the group consisting of: hydrogen, aryl, $C_3-C_{10}$ cycloalkyl, $C_2-C_6$ alkenyl, $C_2-C_6$ alkynyl, $R^8O-$, $R^9S(O)_m-$, $R^8C(O)NR^8-$, CN, $NO_2$, $(R^8)_2NC(NR^8)-$, $R^8C(O)-$, $R^8OC(O)-$, $N_3$, $-N(R^8)_2$, $R^9OC(O)NR^8-$ and $C_1-C_6$ alkyl, unsubstituted or substituted by 1–3 groups selected from the group consisting of: halo, aryl, heterocyclyl, $C_3-C_{10}$ cycloalkyl, $C_2-C_6$ alkenyl, $C_2-C_6$ alkynyl, $R^8O-$, $R^9S(O)_m-$, $R^8C(O)NR^8-$, CN, $(R^8)_2NC(NR^8)-$, $R^8C(O)-$, $R^8OC(O)-$, $N_3$, $-N(R^8)_2$ and $R^9OC(O)NR^8-$;

$R^3$ and $R^4$ are independently selected from the group consisting of: H, F, Cl, Br, $-N(R^8)_2$, $CF_3$, $NO_2$, $R^8O-$, $R^9S(O)_m-$, $CF_3(CH_2)_nO-$, $R^8C(O)NH-$, $H_2NC(NH)-$, $R^8C(O)-$, $R^8OC(O)-$, $N_3$, CN, $R^9OC(O)NR^8-$, substituted and unsubstituted $C_1-C_{20}$ alkyl, substituted and unsubstituted aryl and substituted or unsubstituted heterocyclyl;

$A^3$ is: $-NR^5C(O)-$;

$A^4$ is selected from O, S(O)m, wherein m is 0, 1 or 2, $NR^5$, OC(O), C(O)O, $NR^5S(O)_m$ and $S(O)_mNR^5$, with m as defined above and $R^5$ selected from the group consisting of: hydrogen, unsubstituted or substituted aryl, unsubstituted or substituted heterocyclyl, unsubstituted or substituted $C_3-C_{10}$ cycloalkyl, and $C_1-C_6$ alkyl unsubstituted or substituted with 1–3 members selected from the group consisting of: unsubstituted or substituted aryl, unsubstituted or substituted heterocyclyl, unsubstituted or substituted $C_3-C_{10}$ cycloalkyl, $N(R^8)_2$, $CF_3$, $NO_2$, $(R^8)O-$, $(R^9)S(O)_m-$, $(R^8)C(O)NH-$, $H_2N-C(NH)-$, $(R^8)C(O)-$, $(R^8)OC(O)-$, $N_3$, CN $(R^9)OC(O)NR^8-$;

$R^6$ and $R^7$ are independently selected from the group consisting of: hydrogen, aryl, heterocyclyl, $C_3-C_{10}$ cycloalkyl, $C_2-C_6$ alkenyl, $C_2-C_6$ alkynyl, $C_{1-6}$ perfluoroalkyl, F, Cl, Br, $R^8O-$, $R^9S(O)_m-$, $R^8C(O)NR^8-$, CN, $NO_2$, $(R^8)_2NC(NR^8)-$, $R^8C(O)-$, $R^8OC(O)-$, $N_3$, $-N(R^8)_2$, $R^9OC(O)NR^8-$ and $C_1-C_6$ alkyl unsubstituted or substituted by 1–3 groups selected from: aryl, heterocyclyl, $C_3-C_{10}$ cycloalkyl, $C_2-C_6$ alkenyl, $C_2-C_6$ alkynyl, perfluoroalkyl, F, Cl, Br, $R^8O-$, $R^9S(O)_m-$, $R^8C(O)NR^8-$, CN, $(R^8)_2NC(NR^8)-$, $R^8C(O)-$, $R^8OC(O)-$, $N_3$, $-N(R^8)_2$ and $R^9OC(O)NR^8-$;

each $R^8$ is independently selected from hydrogen, $C_1-C_6$ alkyl, aryl and aralkyl;

each $R^9$ is independently selected from $C_1-C_6$ alkyl and aryl;

$A^1$ and $A^2$ are independently selected from the group consisting of: a bond, $-CH=CH-$, $-C\equiv C-$, $-C(O)-$, $-C(O)NR^8-$, $-NR^8C(O)-$, $-O-$, $-N(R^8)-$, $-S(O)_2N(R^8)-$, $-N(R^8)S(O)_2-$, and $S(O)_m$;

V is selected from the group consisting of: hydrogen, heterocyclyl, aryl, $C_1-C_{20}$ alkyl wherein from 0 to 4 carbon atoms are replaced with a heteroatom selected from O, S, and N, and $C_2-C_{20}$ alkenyl, provided that V is not hydrogen if $A^1$ is $S(O)_m$ and V is not hydrogen if $A^1$ is a bond, n is 0 and $A^2$ is $S(O)_m$;

W represents heterocyclyl;

Y represents aryl;

each n and p independently represents 0, 1, 2, 3 or 4;

q is 1, 2, 3 or 4;

r is 0 to 5, provided that r is 0 when V is hydrogen, and t is 0 or 1.

DETAILED DESCRIPTION OF THE INVENTION

The compounds of this invention are useful in the inhibition of farnesyl-protein transferase and the farnesylation of the oncogene protein Ras, and thus are useful for the treatment of cancer.

The compounds of the present invention may have asymmetric centers and occur as racemates, racemic mixtures and as individual diastereomers, with all possible isomers, including optical isomers, being included in the present invention.

When any variable (e.g. aryl, heterocycle, $R^1$, $R^2$ etc.) occurs more than one time in any constituent, each definition is independent.

The term "alkyl" and the alkyl portion of alkoxy, aralkyl and similar terms, is intended to include branched and straight-chain saturated aliphatic hydrocarbon groups having the specified number of carbon atoms, or 1–6 carbon atoms if unspecified. Cycloalkyl means 1–2 carbocyclic rings which are saturated and contain from 3–10 atoms.

"Halogen" or "halo" as used herein means fluoro, chloro, bromo and iodo.

As used herein, "aryl" and the aryl portion of aralkyl, are intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl. A preferred aralkyl group is benzyl.

The terms heterocyclyl, heterocycle and heterocyclic, as used herein, mean a 5- to 7-membered monocyclic or 8- to 11-membered bicyclic heterocyclic rings, either saturated or unsaturated, aromatic, partially aromatic or non-aromatic, and which consist of carbon atoms and from one to four heteroatoms selected from the group consisting of N, O, and S. Thus, it includes any bicyclic group in which any of the above-defined heterocyclic rings is fused to a benzene ring. The ring or ring system may be attached at any heteroatom or carbon atom which results in a stable structure, and may contain 1–3 carbonyl groups. Examples of such heterocycles include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

"Heteroaryl" is a subset of heterocyclic, and means a monocyclic or bicyclic ring system, with up to 7 members in each ring, wherein at least one ring is aromatic and wherein from one to four carbon atoms are replaced by heteroatoms selected from the group consisting of N, O, and S. Examples include benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl and thienyl.

Preferably, W is heterocyclyl selected from imidazolinyl, imidazolyl, oxazolyl, pyrazolyl, pyrrolidinyl, thiazolyl and pyridyl. More preferably, W is selected from imidazolyl and pyridyl.

Preferably, m is 2.

Preferably n and p are 0, 1, 2 or 3.

Preferably t is 1.

A subset of compounds of the invention is represented by formula Ia:

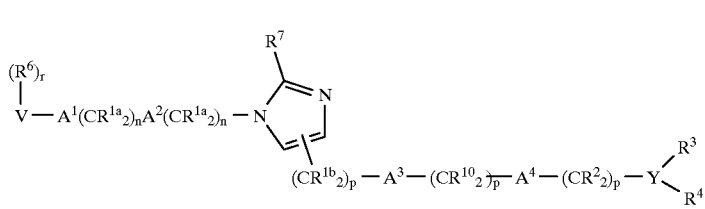

Ia

Lines drawn into ring systems from substituents indicate that the bond may be attached to any of the substitutable ring atoms.

The term "substituted" as used, e.g., with substituted alkyl, substituted aryl, substituted heterocyclyl and substituted cycloalkyl, means alkyl, aryl, heterocyclyl and cycloalkyl groups, respectively, having from 1–3 substituents which are selected from: halo, aryl, heterocyclyl, $C_{3-10}$ cycloalkyl, $C_{2-6}$ alkenyl, $C_{2-6}$ alkynyl, $R^8O-$, $R^9S(O)_m-$, $R^8C(O)NR^8-$, CN, $(R^8)_2NC(NR^8)-$, $R^8C(O)-$, $R^8OC(O)-$, $N_3$, $-N(R_8)_2$ and $R^9OC(O)NR^8-$.

Preferably 1–2 groups are present on substituted alkyl, substituted aryl, substituted heterocyclyl and substituted cycloalkyl, which are selected from: halo, aryl, $R^8O-$, CN, $R^8C(O)-$ and $-N(R^8)_2$.

Preferably, $R^{1a}$, $R^{1b}$ and $R^2$ are independently selected from: hydrogen, $-N(R^8)_2$, $R^8C(O)NR^8-$ or unsubstituted or substituted $C_1-C_6$ alkyl wherein the substituent on the substituted $C_1-C_6$ alkyl is selected from unsubstituted or substituted aryl, $-N(R^8)_2$, $R^8O-$ and $R^8C(O)NR^8-$.

Preferably, $R^3$ and $R^4$ are selected from: hydrogen and $C_1-C_6$ alkyl.

Preferably, $A^3$ represents $-NR^5C(O)-$, wherein $R^5$ represents hydrogen.

Preferably, $R^6$ represents CN, $NO_2$ or $R^8O-$.

Preferably $R^7$ represents hydrogen, unsubstituted or substituted $C_1-C_6$ alkyl.

Preferably, $R^8$ represents H or $C_{1-6}$ alkyl, and $R^9$ is $C_{1-6}$ alkyl.

Preferably, $A^1$ and $A^2$ are independently selected from: a bond, $-C(O)NR^8-$, $-NR^8C(O)-$, $-O-$, $-N(R^8)-$, $-S(O)_2N(R^8)-$ and $-N(R^8)S(O)_2-$.

Preferably, V is selected from hydrogen, heterocyclyl and aryl. More preferably V is phenyl.

wherein:
$R^3$, $R^4$, $A^3$, $A^4$, Y, $R^8$, $R^9$, m, n, p and r are as originally defined;

each $R^{1a}$, $R^{1b}$, $R^2$ and $R^{10}$ is independently selected from hydrogen and $C_1-C_6$ alkyl;

$R^5$ is selected from the group consisting of: hydrogen and $C_1-C_6$ alkyl, unsubstituted or substituted with 1–3 members selected from the group consisting of: unsubstituted or substituted aryl, unsubstituted or substituted heterocyclyl, unsubstituted or substituted $C_3-C_{10}$ cycloalkyl, $-N(R^8)_2$, $-CF_3$, $-NO_2$, $(R^8)O-$, $(R^9)S(O)_m-$, $(R^8)C(O)NH-$, $H_2NC(NH)-$, $(R^8)C(O)-$, $(R^8)OC(O)-$, $N_3$, CN and $(R^9)OC(O)NR^8-$;

$R^6$ and $R^7$ are independently selected from: hydrogen, $C_1-C_6$ alkyl, $C_2-C_6$ alkenyl, $C_2-C_6$ alkynyl, $C_1-C_6$ perfluoroalkyl, F, Cl, $R^8O-$, $R^8C(O)NR^8-$, CN, $NO_2$, $(R^8)_2N-C(NR^8)-$, $R^8C(O)-$, $R^8OC(O)-$, $-N(R^8)_2$, or $R^9OC(O)NR^8-$, and $C_1-C_6$ alkyl substituted by $C_1-C_6$ perfluoroalkyl, $R^8O-$, $R^8C(O)NR^8-$, $(R^8)_2N-C(NR^8)-$, $R^8C(O)-$, $R^8OC(O)-$, $-N(R^8)_2$ and $R^9OC(O)NR^8s-$;

$A^1$ and $A^2$ are independently selected from: a bond, $-CH=CH-$, $-C\equiv C-$, $-C(O)-$, $-C(O)NR^8-$, O, $-N(R^8)-$ and $S(O)_m$;

and V is selected from: hydrogen; aryl; heterocyclyl selected from pyrrolidinyl, imidazolyl, pyridinyl, thiazolyl, pyridonyl, 2-oxopiperidinyl, indolyl, quinolinyl, isoquinolinyl and thienyl; $C_1-C_{20}$ alkyl wherein from 0 to 4 carbon atoms are replaced with a a heteroatom selected from O, S, and N, and $C_2-C_{20}$ alkenyl, provided that V is not hydrogen if $A^1$ is $S(O)_m$ and V is not hydrogen if $A^1$ is a bond and $A^2$ is $S(O)_m$.

A second subset of compounds of the present invention is represented by formula Ib:

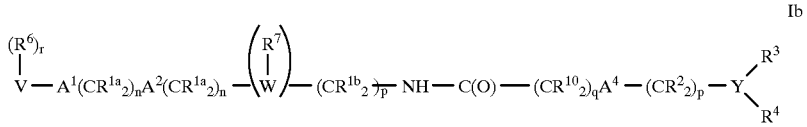

wherein:

$R^{1a}$, $R^{1b}$, $R^2$, $R^{10}$, $A^1$, $A^2$, $A^4$, Y, $R^3$, $R^4$, $R^5$, $R^6$, $R^8$, $R^9$, m, n, p, q and r are as originally defined;

$R^7$ is selected from: hydrogen and $C_1$–$C_6$ alkyl;

V is selected from: hydrogen, heterocyclyl selected from pyrrolidinyl, imidazolyl, pyridinyl, thiazolyl, pyridonyl, 2-oxopiperidinyl, indolyl, quinolinyl, isoquinolinyl, and thienyl, aryl, $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$; and W represents heterocyclyl selected from pyrrolidinyl, pyridinyl, thiazolyl, pyridonyl, 2-oxopiperidinyl, indolyl, quinolinyl and isoquinolinyl.

A third embodiment of the invention is described in accordance with formula Ic:

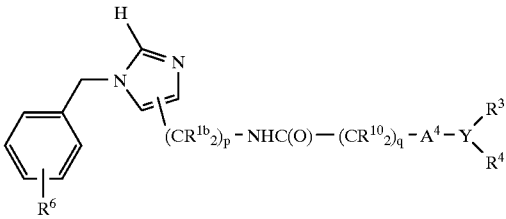

wherein:
each $R^{1b}$ and $R^{10}$ is independently selected from hydrogen and $C_1$–$C_6$ alkyl;
$R^3$, $R^4$, $A^4$, $R^8$, $R^9$, m, p, q and Y are as originally defined; and $R^6$ is selected from the group consisting of: hydrogen, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$— and $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$ or $R^9OC(O)NR^8$—.

Specific examples of compounds of the invention are:

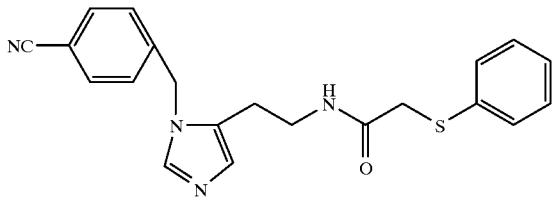

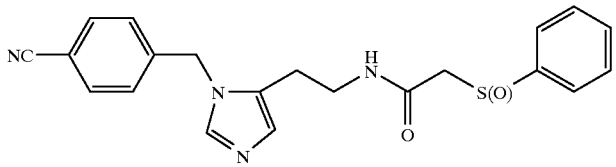

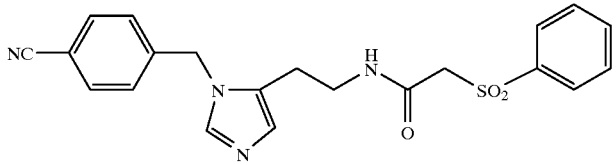

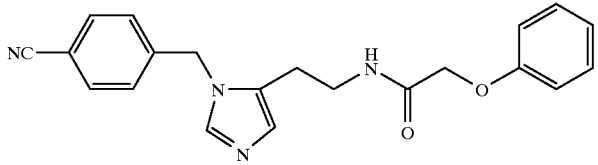

-continued
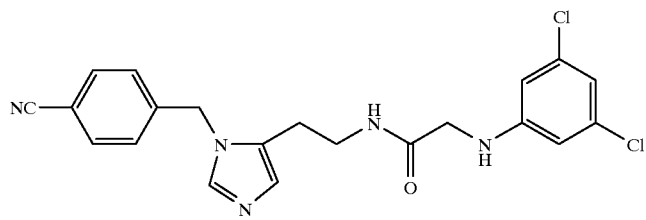
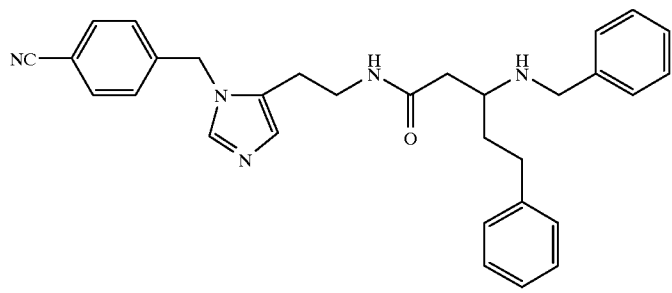
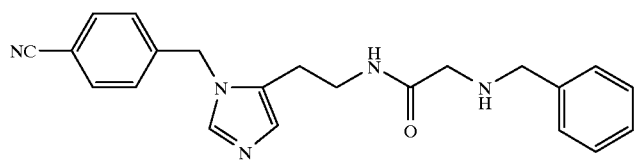
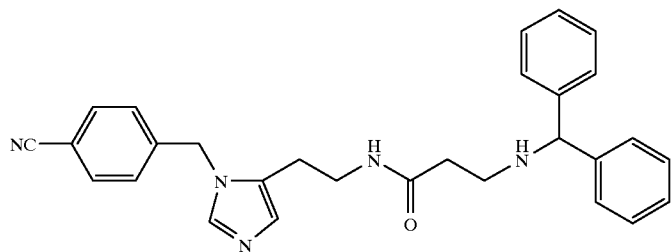
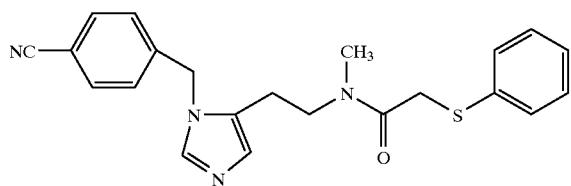
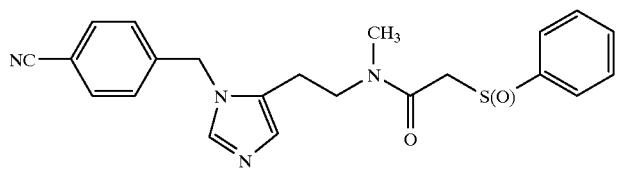
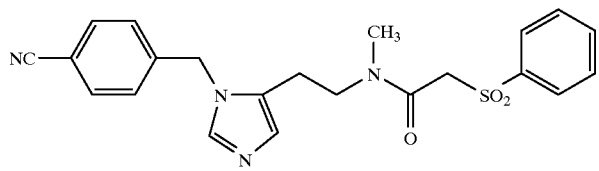

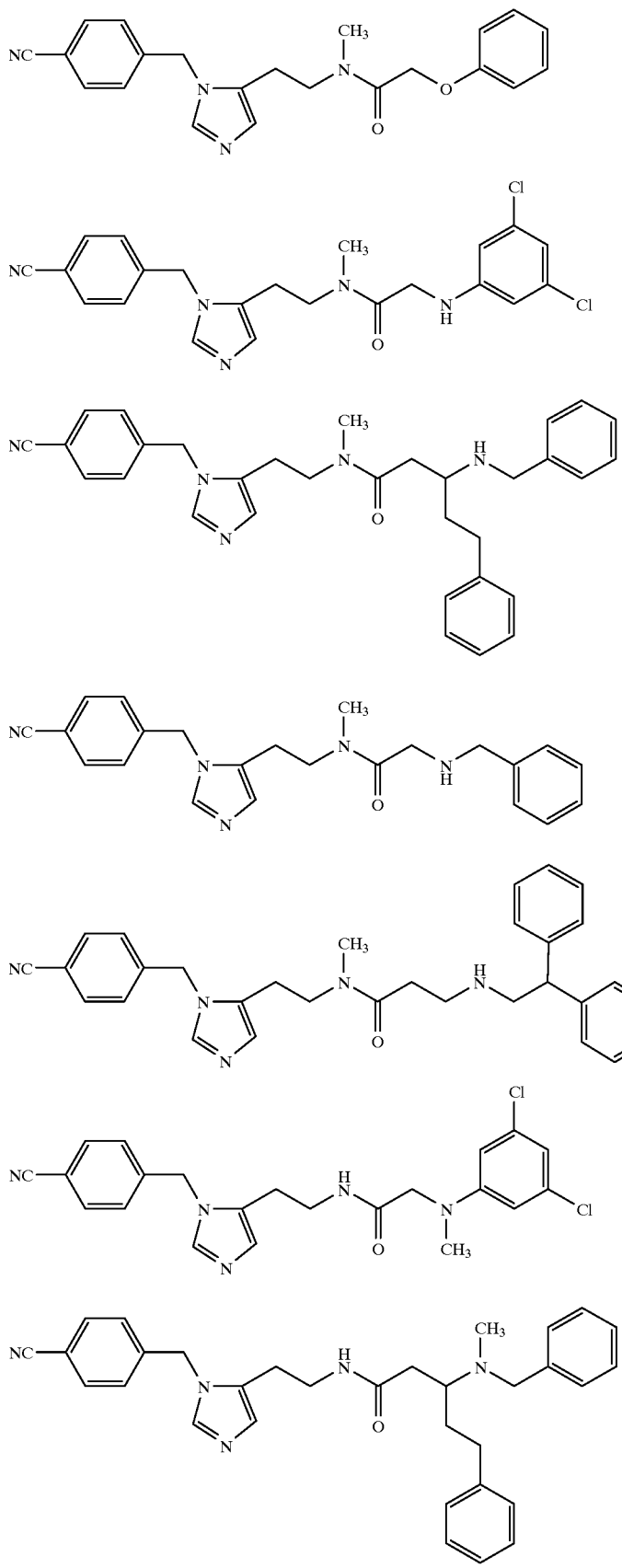

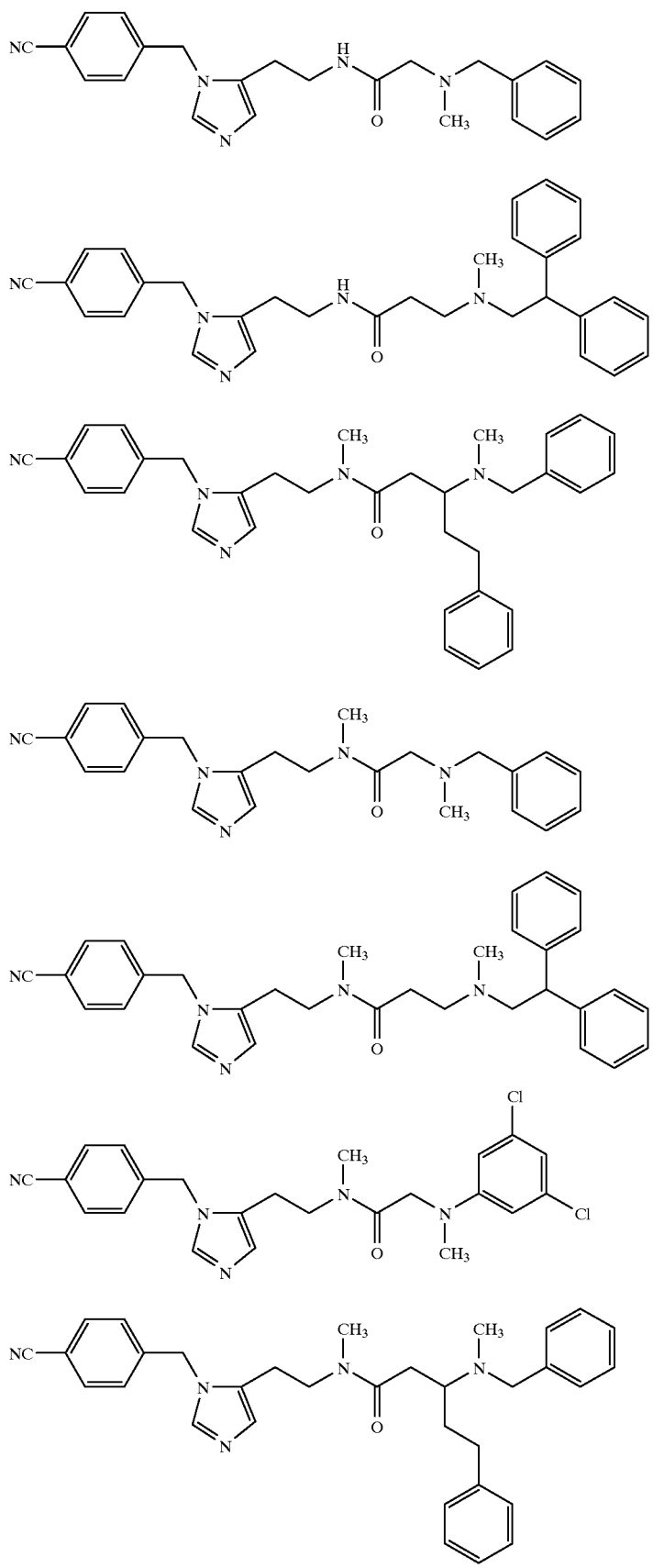

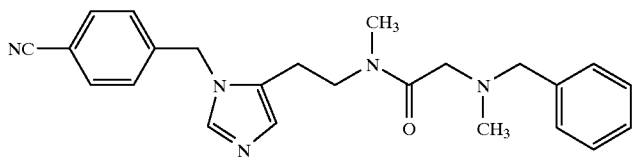

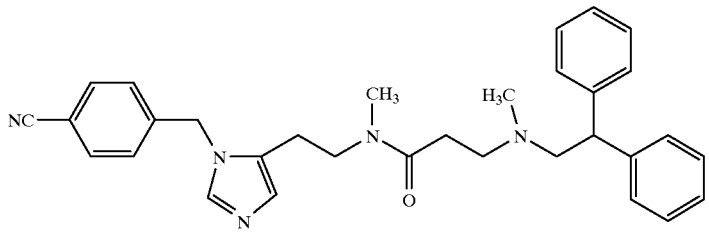

and the pharmaceutically acceptable salts thereof.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in Schemes 1–12, in addition to other standard manipulations such as ester hydrolysis, cleavage of protecting groups, etc., as may be known in the literature or exemplified in the experimental procedures. Substituents R' and R'CH$_2$, as shown in the Schemes, represent the substituents $R^8$, $R^5$ and others, depending on the compound of the instant invention that is being synthesized. The variable p' represents p-1.

These reactions may be employed in a linear sequence to provide the compounds of the invention or they may be used to synthesize fragments which are subsequently joined by the alkylation reactions described in the Schemes.

Synopsis of Synthesis Schemes 1–14

The requisite intermediates are commercially available or can be prepared according to literature procedures. Schemes 1–4 incorporate a preferred aspect of the invention, wherein the variable W is present as a imidazolyl moiety that is substituted with a suitably substituted benzyl group. However, other values of W are applicable here as well. Substituted protected imidazole alkylamines I (Scheme 1) can be prepared by methods such as those described by J. C. Emmett et al., *J. Med. Chem.*, 1982, 25, 1168–1174 and from substituted protected imidazoles which can be prepared by methods such as those described by F. Schneider, Z. Physiol. Chem., 3:206–210 (1961) and C. P. Stewart, Biochem. Journal, 17:130–133(1923). Generally the heteroaryl alkylamine or similar intermediate can be reacted with a linking moiety through the displacement of a leaving group, such as a halo group, from an acyl moiety, in a suitable base with an aprotic solvent. The group

can likewise be coupled to the chain by displacement of a leaving group, e.g., a halo group.

When a thioether linkage is present, such as in Scheme 2, the sulfur can be oxidized to a sulfoxide or sulfone using a suitable oxidizing agent.

When $A^4$ represents an amino or ether linkage, the amino or ether linkage can similarly be formed as in Schemes 3 or 4, respectively.

Schemes 5–8 illustrate syntheses of suitably substituted amines wherein the variable W is present as a pyridyl moiety. Similar synthetic strategies for preparing alkanols that incorporate other heterocyclic moieties for variable W are also suitable.

The diamine IX can be derived from the aldehyde IV as shown in Scheme 9. The aldehyde IV is first reductively aminated and then can be debenzylated to give the amine VI. Coupling with a defunctionalized compound such as bromo acetylbromide in a polar solvent such as DMF with an organic base (e.g. triethylamine) followed bv addition of an arylthiol VII yields VIII. Deprotection affords the instant compound IX.

As shown in Scheme 10, Compound IX can further be selectively protected to obtain X which can subsequently be reductively alkylated with a second aldehyde, such as XI, to obtain XII. Removal of the protecting group (to XIII), and conversion to cyclized products such as the dihydroimidazole XIV can be accomplished by literature procedures.

If the aminoalkanol XVI (derived by reduction of the amino acid XV using standard procedures) is coupled under conditions previously described one obtains an alcohol such as XVII (Scheme 11). The alcohol can be oxidized under standard conditions to e.g. an aldehyde XVIII, which can then be reacted with a variety of organometallic reagents such as Grignard reagents, to obtain secondary alcohols such as XIX. In addition, the fully deprotected amino alcohol XX (Scheme 12) can be reductively alkylated (under conditions described previously) with a variety of aldehydes to obtain secondary amines, such as XXI, or tertiary amines.

The Boc protected amino alcohol XVII can also be utilized to synthesize 2-aziridinylmethylamides such as XXII (Scheme 13). Treating XVII with 1,1'-sulfonyldiimidazole and sodium hydride in a solvent such as dimethylformamide leads to the formation of aziridine XXII. The aziridine may be reacted with a nucleophile, such as a thiol, in the presence of base to yield the ring-opened product XXIII. Deprotection then affords XXIV.

In addition, the diamine XXIX can be derived from amino acids such as O-alkylated tyrosines XXVI, according to standard procedures, as shown in Scheme 14. Intermediate XXIX is first coupled with a difunctionalized compound such as bromo acetylbromide followed by addition of an arylthiol VII (as described above) to yield XXX. When R' is an aryl group, XXX can first be hydrogenated to unmask the phenol, and the amine group deprotected with acid to produce XXXII. Alternatively, the amine protecting group in XXX can be removed, and O-alkylated phenolic amines such as XXXI produced.

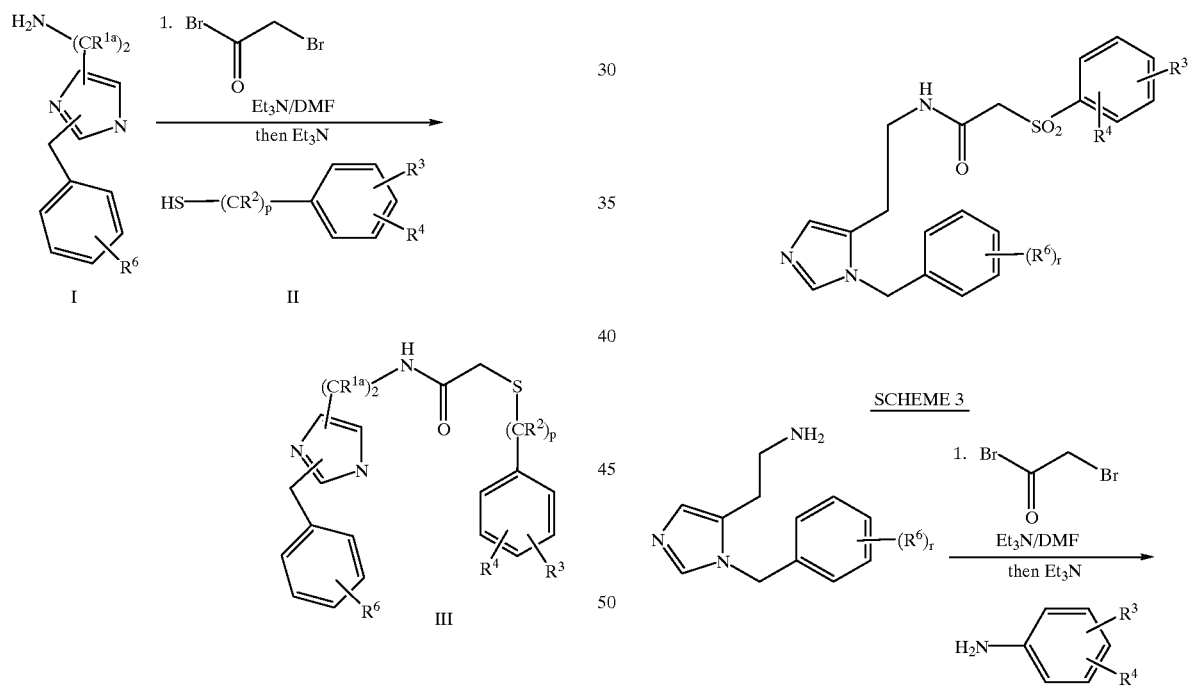

SCHEME 1

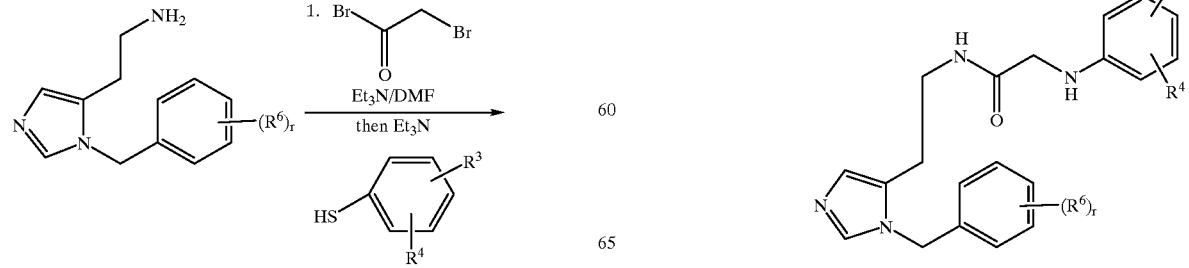

SCHEME 2

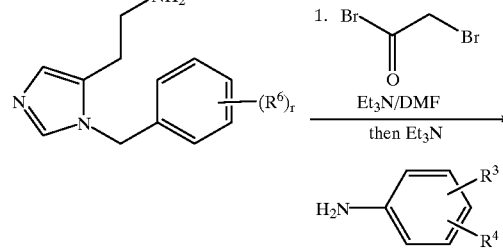

SCHEME 3

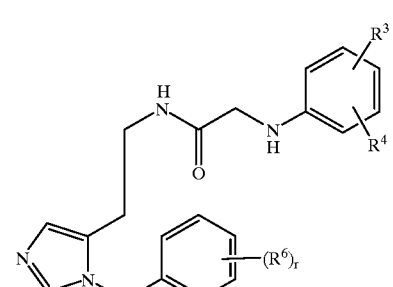

SCHEME 4
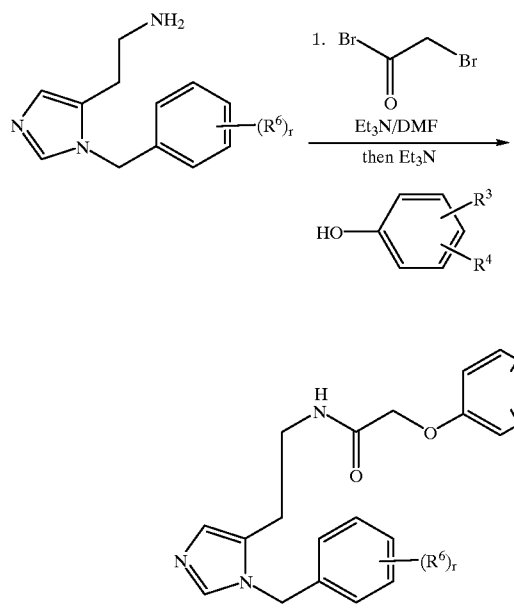
SCHEME 5
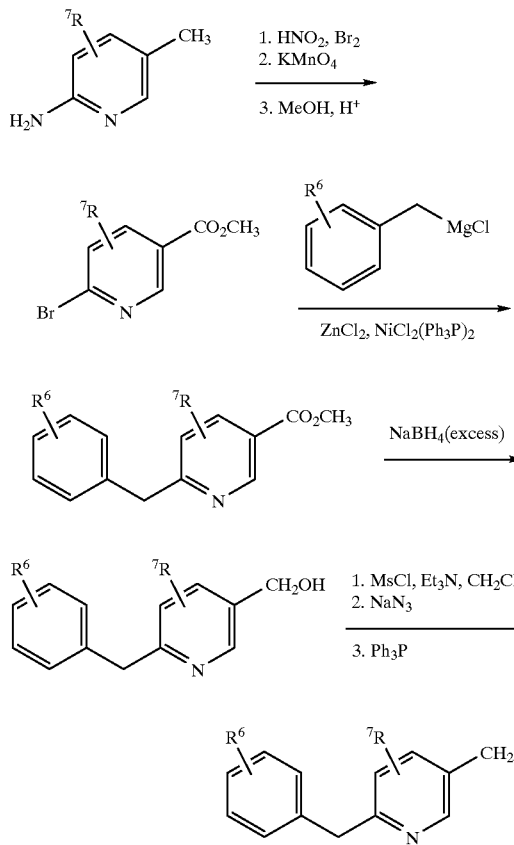
SCHEME 6
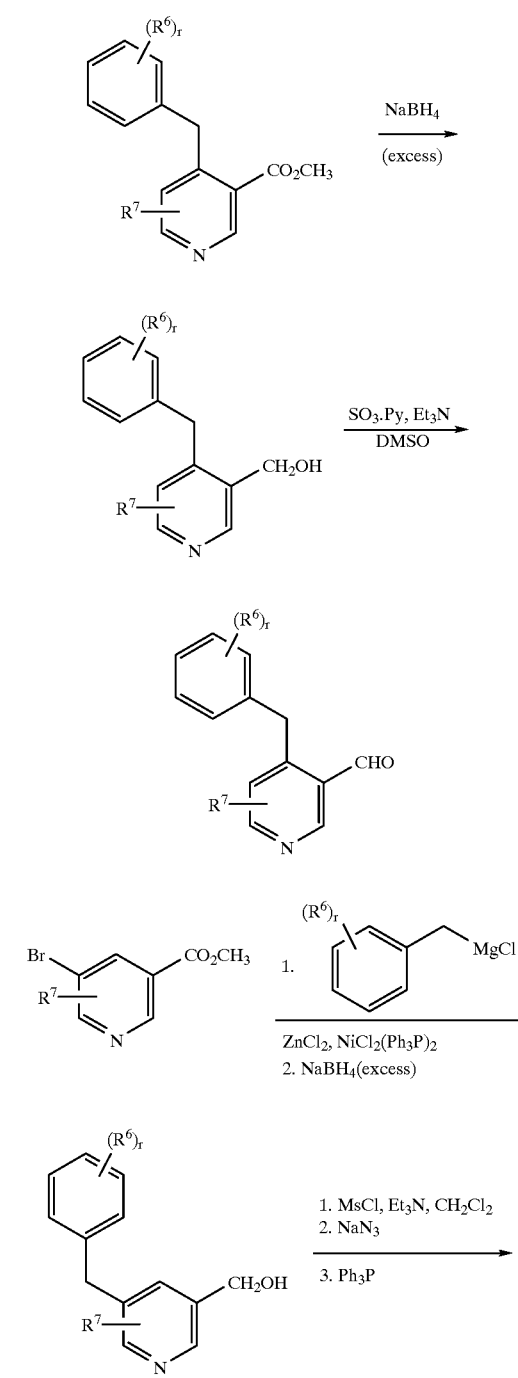

-continued
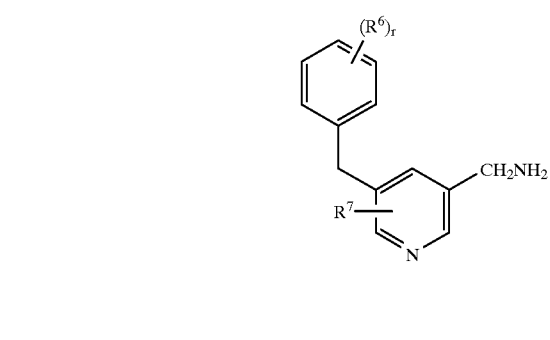
SCHEME 7
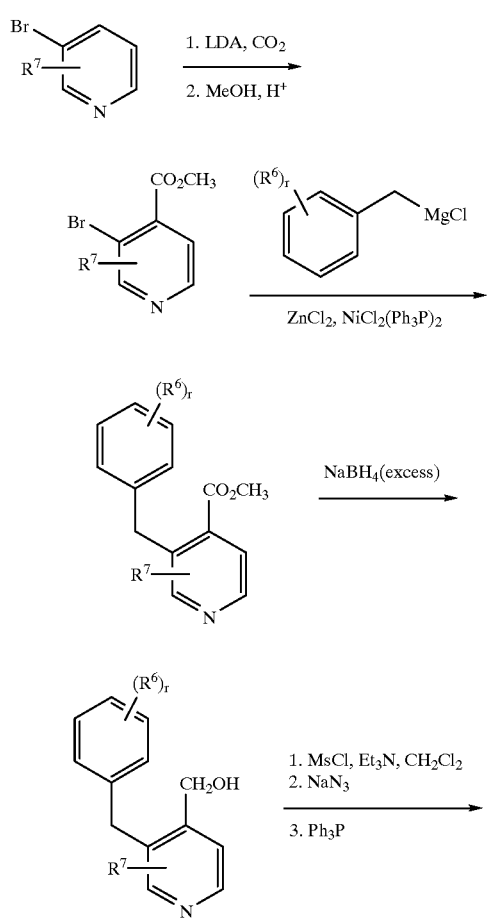
SCHEME 8
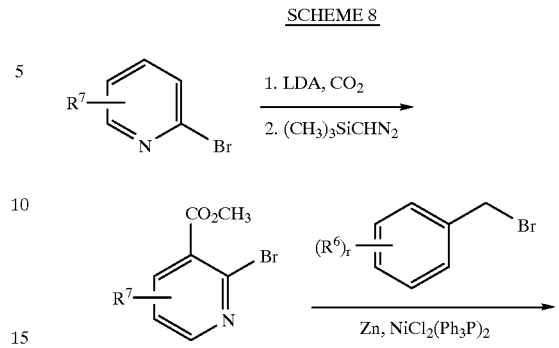
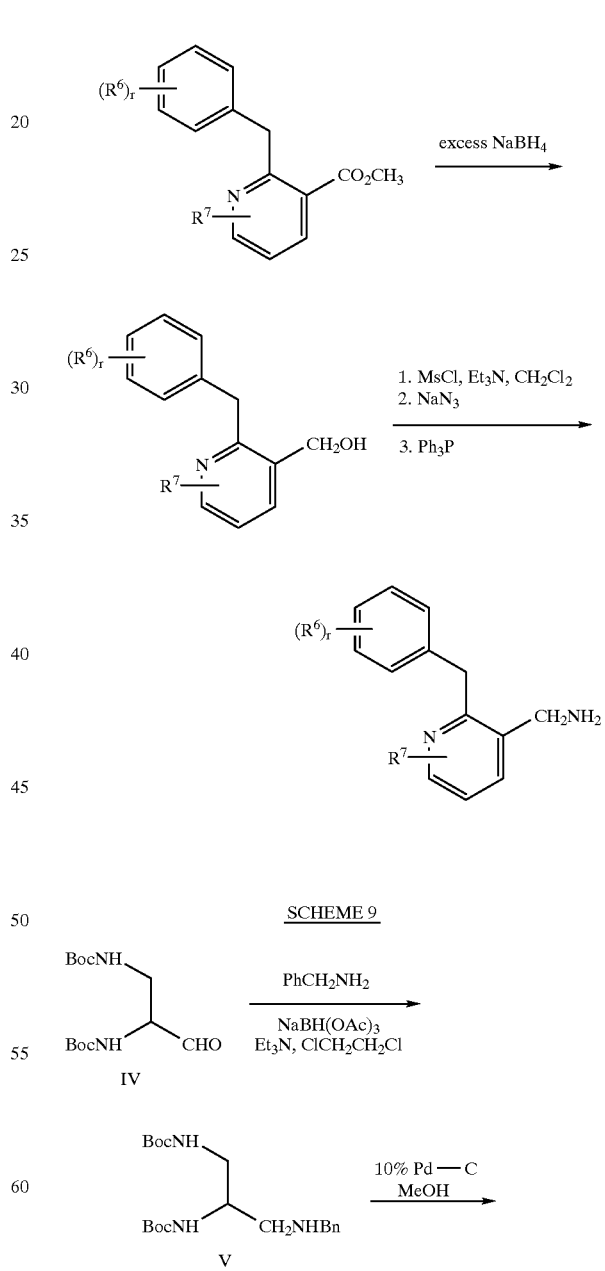
SCHEME 9

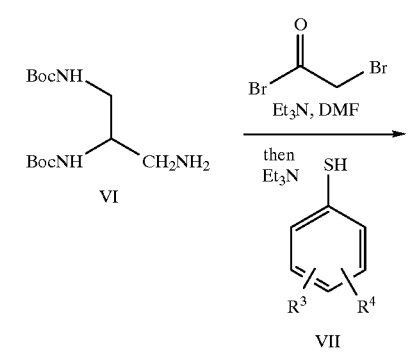
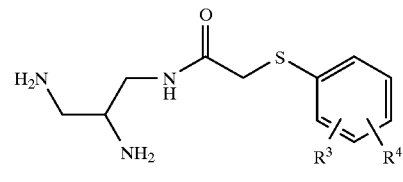
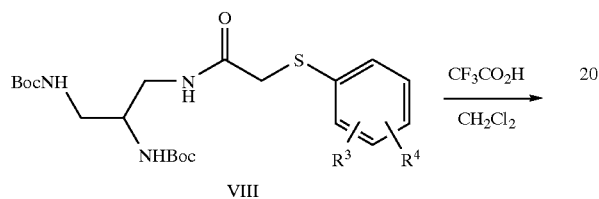
SCHEME 10
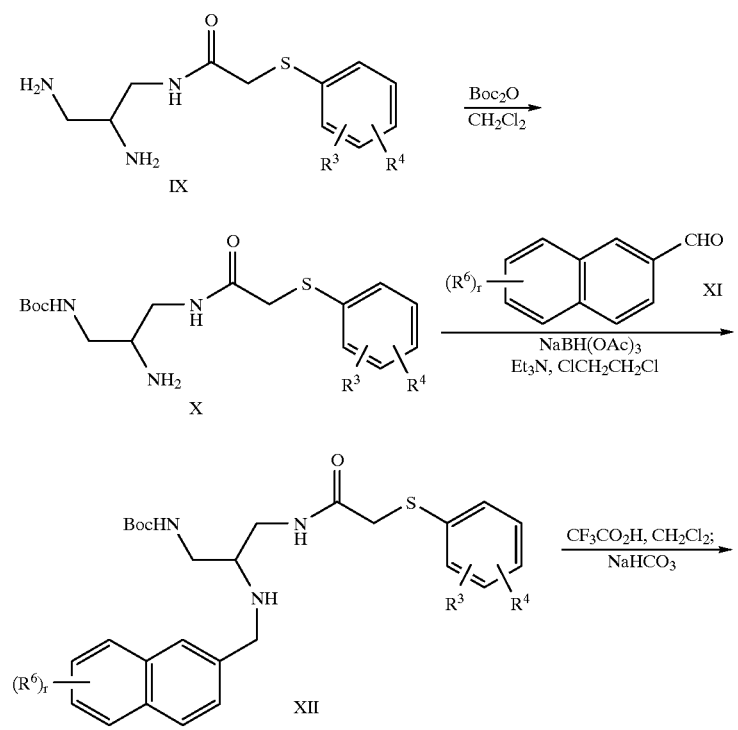

-continued
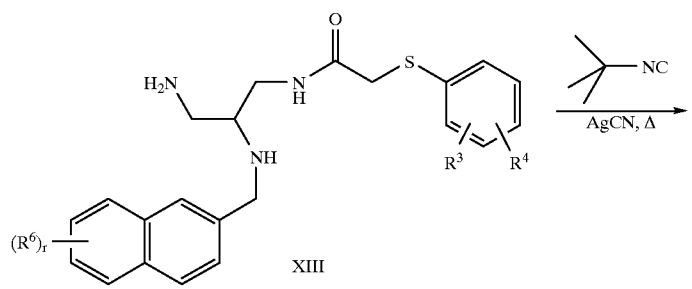
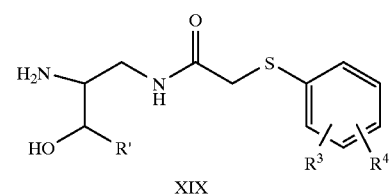
SCHEME 11
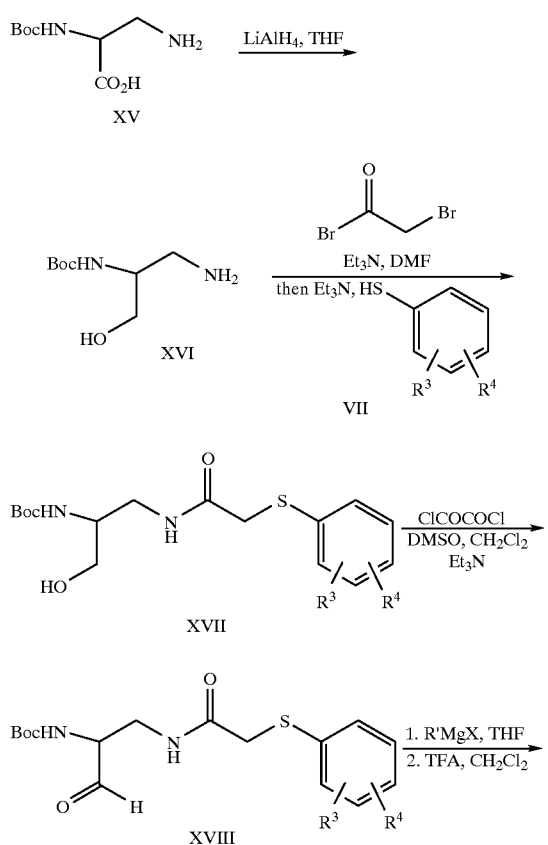
SCHEME 12
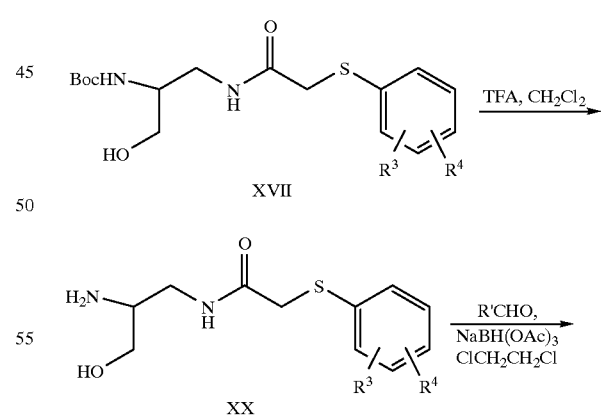

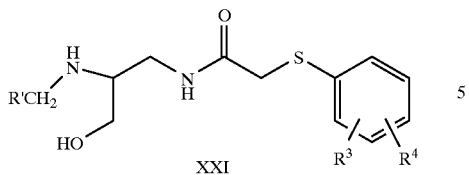
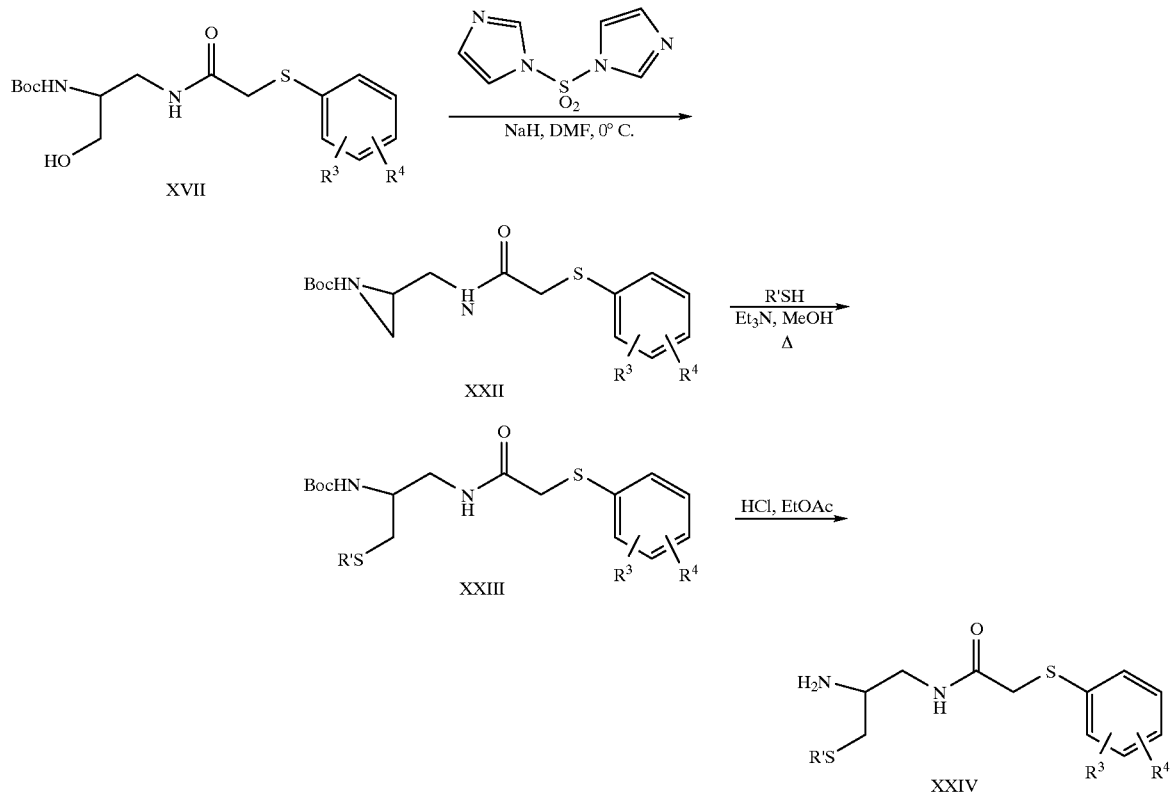
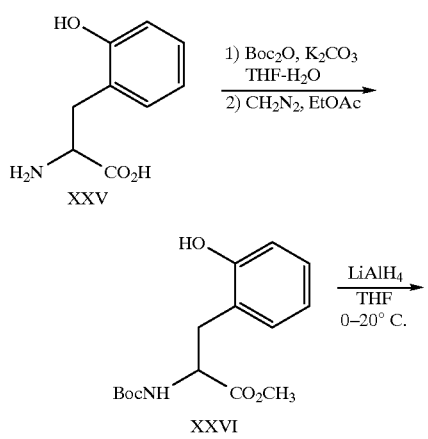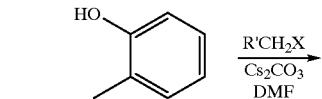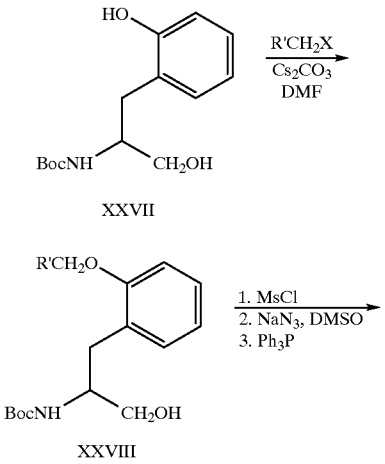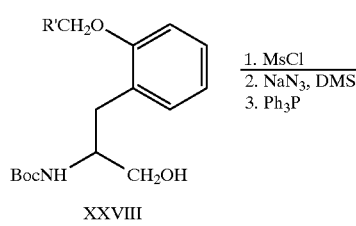

-continued

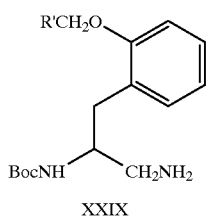

XXIX

The instant compounds are useful in the treatment of cancer. Cancers which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and farnesylation of the oncogene protein Ras. The instant compounds may also inhibit tumor angiogenesis, thereby affecting the growth of tumors (J. Rak et al. *Cancer Research*, 55:4575–4580 (1995)). Such anti-antigenic properties of the instant compounds may also be useful in the treatment of certain forms of blindness related to retinal vascularization.

The compounds of this invention are also useful for inhibiting other diseases where Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, in the form of a pharmaceutical composition, which is comprised of a compound of formula I in combination with a pharmaceutically acceptable carrier. The compounds can be administered orally, topically, rectally, vaginally transdermally or parenterally, including the intravenous, intramuscular, intraperitoneal and subcutaneous routes of administration.

For oral use, the compound is administered, for example, in the form of tablets or capsules, or as a solution or suspension. In the case of tablets for oral use, carriers which are commonly used include lactose and corn starch; lubricating agents, such as magnesium stearate, are commonly added. For oral administration in capsule form, diluents also include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, the pH of the solution is suitably adjusted and the product is buffered. For intravenous use, the total concentration is controlled to render the preparation substantially isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ a compound of this invention substantially within the dosage range described below and other pharmaceutically active agent(s) typically within the acceptable dosage range. Compounds of the instant invention may alternatively be used sequentially with known pharmaceutically acceptable agent(s) when a combination formulation is inappropriate.

The daily dosage will normally be determined by the prescribing physician, who may vary the dosage according to the age, weight, and response of the individual patient, as well as the severity of the patient's condition.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLE 1

4-CYANOBENZYL HISTAMINE

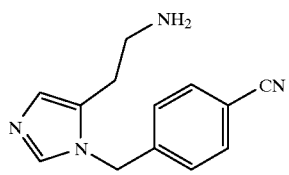

$N^\Gamma$-Pivaloyloxymethyl-$N^\alpha$-phthaloylhistamine (4.55 g, 12.8 mmol; prepared as previously described (J. C. Emmett, F. H. Holloway, and J. L. Turner, *J. Chem. Soc., Perkin Trans.* 1, 1341, (1979)) and α-bromo-p-tolunitrile (3.77 g, 19.2 mmol) were dissolved in acetonitrile (70 mL). The solution was heated at 55° C. for 4 h, cooled to room temperature, and filtered to remove the white solid. The acetonitrile (30 mL) was concentrated to ½ its volume under reduced pressure and the solution was heated at 55° C. overnight. The solution was cooled and filtered to give a white solid. The volume of the filtrate was reduced to 10 mL, the solution was heated at 55° C. for 1 hr, then cooled to room temperature, diluted with EtOAc (25 mL) and filtered to obtain additional white solid. The solids were combined, dried, and used without further purification.

1-Pivaloyloxymethyl-3-(4-cyanobenzyl)-4-(2-phthalimidoethyl)imidazolium bromide (6.13 g, 11.1 mmol) in methanol (100 mL) was saturated with ammonia gas while the temperature was maintained below 30° C. The solution was stirred for 1 hr, concentrated to dryness, and extracted with $CH_2Cl_2$ (3×200 mL), dried ($MgSO_4$), concentrated, and chromatographed (silica gel, 10:90:1 $MeOH/CH_2Cl_2/NH_4OH$) to give 4-cyanobenzyl-$N^\alpha$-phthaloylhistamine.

4-Cyanobenzyl-$N^\alpha$-phthaloylhistamine (1.64 g, 4.61 mmol), and hydrazine (1.46 mL, 46.1 mmol) were dissolved in absolute EtOH (70 mL). The solution was concentrated after 1 hr and filtered to remove a white precipitate which was washed several times with EtOH. The filtrate was concentrated and the residue was chromatographed (silica gel, 10:90:1 $MeOH/CH_2Cl_2/NH_4OH$) to give the title compound.

EXAMPLE 2

2-PHENYLTHIO-N-2-{1-(4-CYANOBENZYL) IMIDAZOL-5-YL}ETHYL ACETAMIDE

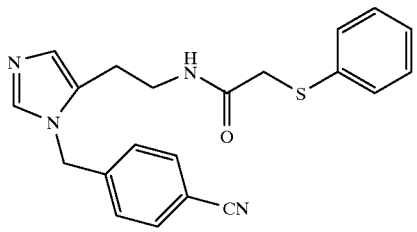

To a solution of 4-cyanobenzyl histamine (100 mg, 0.33 mmol) and $Et_3N$ (92 μL, 0.66 mmol) in DMF (8 mL) at room temperature was added 2-bromoacetyl bromide (35 μL, 0.4 mmol). After 15 min., thiophenol (80 μL, 0.72 mmol) and $Et_3N$ (92 μL, 0.66 mmol) were added and the mixture stirred a further 1 h. The mixture was poured into $H_2O$ and EtOAc, extracted with EtOAc (3×), washed with brine, dried ($MgSO_4$), filtered and evaporated to give an oil. Purification by column chromatography (silica gel; 5% $MeOH/CHCl_3$) gave a clear oil which was treated with 1N HCl in ether and the solvent removed in vacuo to give the title compound (hydrochloride) as a white solid.

Analysis for $C_{21}H_{20}N_4OS \cdot 1.2HCl \cdot 0.15H_2O$; Calcd. C, 59.63; H, 5.12; N, 13.25; Found C, 59.66; H, 5.12; N, 13.32

EXAMPLE 3

2-PHENYLTHIO-S-OXIDE-N-2-{1-(4-CYANOBENZYL) IMIDAZOL-5-YL}ETHYL ACETAMIDE

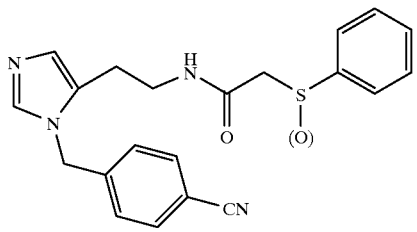

A solution of 2-phenylthio-N-2-{1-(4-cyanobenzyl) imidazol-5-yl}ethyl acetamide (Example 1; 91 mg, 0.24 mmol) in $CH_2Cl_2$ (5 mL) was treated with m-CPBA (83.5 mg;~0.48 mmol) and the mixture stirred at room temperature for 1 h. The solution was poured into saturated $NaHCO_3$ solution, extracted with $CH_2Cl_2$ (3×), washed with brine, dried ($MgSO_4$) and the concentrated in vacuo. Column chromatography (silica gel; 5% $MeOH/CHCl_3$) yielded an oil which was further purified by preparative HPLC ($H_2O/CH_3CN$ with 0.1% TFA; gradient) collecting the first eluted compound. This solution was lyophilized to afford the title compound as the trifluoroacetic acid salt.

$^1H$ NMR (300 MHz, $CD_3OD$)δ 2.8 (2H, m), 3.5 (2H, m), 3.68 (1H, d, J=13.3 Hz), 3.77 (1H, d, J=13.3 Hz), 5.61 (2H, s), 7.48 (3H, m), 7.58 (3H, m), 7.7 (2H, m), 7.82 (2H, d, J=8.6 Hz), 8.43 (1H, m), 9.01 (1H, s).

EXAMPLE 4

2-PHENYLTHIO-S,S-DIOXIDE-N-2-{1-(4-CYANOBENZYL IMIDAZOL-5-YL}ETHYL ACETAMIDE

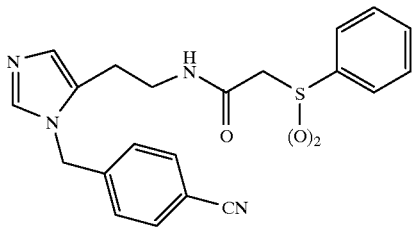

Following the procedure described for Example 2, but collecting the slower eluted compound from the HPLC purification, followed by lyophilization, the title compound was obtained as the trifluoroacetic acid salt.

$^1$H NMR (300 MHz, CD$_3$OD)δ 2.8 (2H, t, J=6.5 Hz), 3.42 (2H, m), 4.11 (2H, s), 5.61 (2H, s), 7.47 (2H, d, J=8.5 Hz), 7.52 (1H, s), 7.63 (2H, m), 7.75 (2H, m), 7.82 (2H, d, J=8.5 Hz), 7.90 (2H, m), 8.49 (1H, m), 9.01 (1H, s).

In Vitro Inhibition of Ras Farnesyl Transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

In Vivo Ras Farnesylation Assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/ SDS/0.1M NACl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

In Vivo Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×104 cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound represented by formula I:

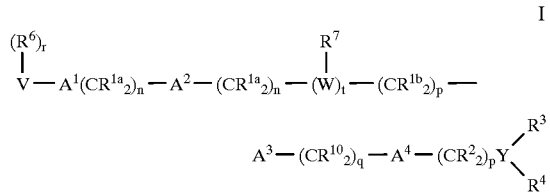

or a pharmaceutically acceptable salt thereof, wherein:

R$^{1a}$, R$^{1b}$, R$^2$ and R$^{10}$ are independently selected from the group consisting of: hydrogen, aryl, C$_3$–C$_{10}$ cycloalkyl, C$_2$–C$_6$ alkenyl, C$_2$–C$_6$ alkynyl, R$^8$O—, R$^9$S(O)$_m$—, R$^8$C(O)NR$^8$—, CN, NO$_2$, (R$^8$)$_2$NC(NR$^8$)—, R$^8$C(O)—, R$^8$OC(O)—, N$_3$, —N(R$^8$)$_2$, R$^9$OC(O)NR$^8$— and C$_1$–C$_6$ alkyl, unsubstituted or substituted by 1–3 groups selected from the group consisting of: halo, aryl, heterocyclyl, C$_3$–C$_{10}$ cycloalkyl, C$_2$–C$_6$ alkenyl, C$_2$–C$_6$ alkynyl, R$^8$O—, R$^9$S(O)$_m$—, R$^8$C(O)NR$^8$—, CN, (R$^8$)$_2$NC(NR$^8$)—, R$^8$C(O)—, R$^8$OC(O)—, N$_3$, —N(R$^8$)$_2$ and R$^9$OC(O)NR$^8$—;

R$^3$ and R$^4$ are independently selected from the group consisting of: H, F, Cl, Br, —N(R$^8$)$_2$, CF$_3$, NO$_2$, $R^8O$—, $R^9S(O)_m$—, $R^8C(O)NH$—, $H_2NC(NH)$—, $R^8C(O)$—, $R^8OC(O)$—, $N_3$, CN, $R^9OC(O)NR^8$—, substituted and unsubstituted $C_1$–$C_{20}$ alkyl, substituted or unsubstituted aryl and substituted or unsubstituted heterocyclyl;

$A^3$ is: —$NR^5C(O)$—;

$A^4$ is $S(O)_m$, wherein m is 0, 1 or 2;

$R^6$ and $R^7$ are independently selected from the group consisting of: hydrogen, aryl, heterocyclyl, $C_3$–$C_{10}$ cycloalkyl, $C_2$–$C_6$ alkenyl, $C_2$–$C_6$ alkynyl, $C_{1-6}$ perfluoroalkyl, F, Cl, Br, $R^8O$—, $R^9S(O)_m$—, $R^8C(O)NR^8$—, CN, $NO_2$, $(R^8)_2NC(NR^8)$—, $R^8C(O)$—, $R^8OC(O)$—, $N_3$, —$N(R^8)_2$, $R^9OC(O)NR^8$— and $C_1$–$C_6$ alkyl unsubstituted or substituted by 1–3 groups selected from: aryl, heterocyclyl, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $(R^8)_2NC(NR^8)$—, $R^8C(O)$—, $R^8OC(O)$—, $N_3$, —$N(R^8)_2$ and $R^9OC(O)NR^8$—;

each $R^8$ is independently selected from hydrogen, $C_1$–$C_6$ alkyl, aryl and aralkyl;

each $R^9$ is independently selected from $C_1$–$C_6$ alkyl and aryl;

$A^1$ and $A^2$ are independently selected from the group consisting of: a bond, —CH=CH—, —C≡C—, —C(O)—, —C(O)NR^8—, —NR^8C(O)—, —O—, —N(R^8)—, —S(O)_2N(R^8)—, —N(R^8)S(O)_2—, and $S(O)_m$;

V is selected from the group consisting of: hydrogen, heterocyclyl, aryl, $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W represents heterocyclyl;

Y represents aryl;

each n and p independently represents 0, 1, 2, 3 or 4;

q is 1, 2, 3 or 4;

r is 0 to 5, provided that r is 0 when V is hydrogen, and t is 0 or 1.

2. A compound in accordance with claim 1 wherein $R^{1a}$, $R^{1b}$, $R^2$ and $R^{10}$ are independently selected from: hydrogen, —$N(R^8)_2$, $R^8C(O)NR^8$— or unsubstituted or substituted $C_1$–$C_6$ alkyl wherein the substituent on the substituted $C_1$–$C_6$ alkyl is selected from unsubstituted or substituted aryl, —$N(R^8)_2$, $R^8O$— and $R^8C(O)NR^8$—.

3. A compound in accordance with claim 1 wherein $R^3$ and $R^4$ are selected from: hydrogen and $C_1$–$C_6$ alkyl.

4. A compound in accordance with claim 1 wherein $A^3$ represents $NR^5C(O)$, wherein $R^5$ represents hydrogen.

5. A compound in accordance with claim 1 wherein $R^6$ represents CN, $NO_2$ or $R^8O$.

6. A compound in accordance with claim 1 wherein $R^7$ represent hydrogen, unsubstituted or substituted $C_1$–$C_6$ alkyl.

7. A compound in accordance with claim 1 wherein $R^8$ represents H or $C_{1-6}$ alkyl, and $R^9$ is $C_{1-6}$ alkyl.

8. A compound in accordance with claim 1 wherein $A^1$ and $A^2$ are independently selected from: a bond, —C(O)NR^8—, —NR^8C(O)—, —O—, —N(R^8)—, —S(O)_2N(R^8)— and —N(R^8)S(O)_2—.

9. A compound in accordance with claim 1 wherein V is selected from hydrogen, heterocyclyl and aryl.

10. A compound in accordance with claim 1 wherein V is phenyl.

11. A compound in accordance with claim 1 wherein W is heterocyclyl selected from the group consisting of: imidazolinyl, imidazolyl, oxazolyl, pyrazolyl, pyyrolidinyl, thiazolyl and pyridyl.

12. A compound in accordance with claim 11 wherein W is selected from imidazolyl and pyridyl.

13. A compound in accordance with claim 1 wherein m is 2.

14. A compound in accordance with claim 1 wherein n and p are 0, 1, 2 or 3.

15. A compound in accordance with claim 1 wherein t is 1.

16. A compound in accordance with claim 1 represented by formula Ia:

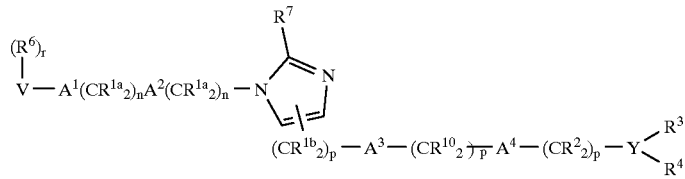

wherein:

$R^3$, $R^4$, $A^3$, $A^4$, Y, $R^8$, $R^9$, m, n, p and r are as originally defined;

each $R^{1a}$, $R^{1b}$, $R^2$ and $R^{10}$ is independently selected from hydrogen and $C_1$–$C_6$ alkyl;

$R^5$ is selected from the group consisting of: hydrogen and $C_1$–$C_6$ alkyl, unsubstituted or substituted with 1–3 members selected from the group consisting of: unsubstituted or substituted aryl, unsubstituted or substituted heterocyclyl, unsubstituted or substituted $C_3$–$C_{10}$ cycloalkyl, —$N(R^8)_2$, $CF_3$, —$NO_2$, $(R^8)O$—, $(R^9)S(O)_m$—, $(R^8)C(O)NH$—, $H_2NC(NH)$—, $(R^8)C(O)$—, $(R^8)OC(O)$—, $N_3$, CN and $(R^9)OC(O)NR^8$—;

$R^6$ and $R^7$ are independently selected from: hydrogen, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$ and $R^9OC(O)NR^8$—;

$A^1$ and $A^2$ are independently selected from: a bond, —CH=CH—, —C≡C—, —C(O)—, —C(O)NR^8—, O, —$N(R^8)$— and $S(O)_m$;

and V is selected from: hydrogen; aryl; heterocyclyl selected from pyrrolidinyl, imidazolyl, pyridinyl, thiazolyl, pyridonyl, 2-oxopiperidinyl, indolyl, quinolinyl, isoquinolinyl and thienyl; $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond and $A^2$ is $S(O)_m$.

17. A compound in accordance with claim 1 represented by formula Ib:

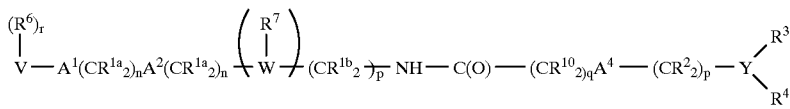

wherein:

$R^{1a}$, $R^{1b}$, $R^2$, $R^{10}$, $A^1$, $A^2$, $A^4$, Y, $R^3$, $R^4$, $R^5$, $R^6$, $R^8$, $R^9$, m, n, p, q and r are as originally defined;

$R^7$ is selected from: hydrogen and $C_1$–$C_6$ alkyl;

V is selected from: hydrogen, heterocyclyl selected from pyrrolidinyl, imidazolyl, pyridinyl, thiazolyl, pyridonyl, 2-oxopiperidinyl, indolyl, quinolinyl, isoquinolinyl, and thienyl, aryl, $C_1$–$C_{20}$ alkyl wherein from 0 to 4 carbon atoms are replaced with a heteroatom selected from O, S, and N, and $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$; and W represents heterocyclyl selected from pyrrolidinyl, pyridinyl, thiazolyl, pyridonyl, 2-oxopiperidinyl, indolyl, quinolinyl and isoquinolinyl.

18. A compound in accordance with claim 1 represented by formula Ic:

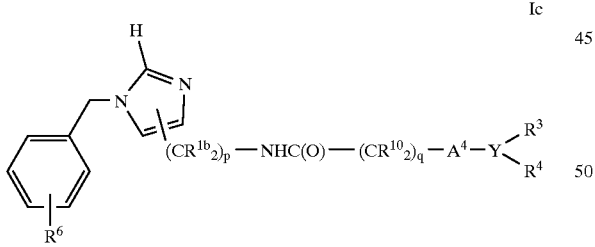

wherein:

each $R^{1b}$ and $R^{10}$ is independently selected from hydrogen and $C_1$–$C_6$ alkyl;

$R^3$, $R^4$, $A^4$, $R^8$, $R^9$, m, p, q and Y are as originally defined;

and $R^6$ is selected from the group consisting of: hydrogen, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$— and $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$ or $R^9OC(O)NR^8$—.

19. A compound in accordance with claim 1 represented by the structural formula:

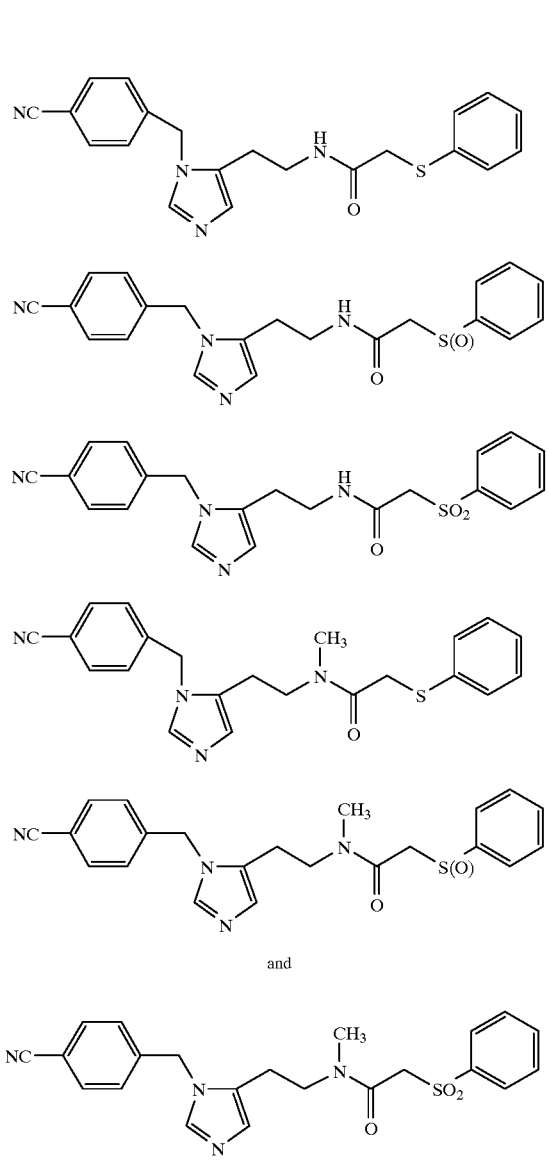

and

20. A pharmaceutical composition which is comprised of a compound in accordance with claim 1 in combination with a pharmaceutically acceptable carrier.

21. A method of treating cancer in a mammalian patient in need of such treatment, comprising administering to said patient an anti-cancer effective amount of a compound of claim 1.

22. A method for inhibiting farnesyl-protein transferase in a mammalian patient in need of such treatment, which comprises administering to said mammal a farnesyl-protein transferase inhibiting amount of a compound of claim 1.

23. A method for treating neurofibromin benign proliferative disorder which comprises administering to a mammal in need thereof a therapeutically effective amount of a compound of claim 1.

24. A method for treating blindness related to retinal vascularization which comprises administering to a mammal in need thereof a therapeutically effective amount of a compound of claim 1.

25. A method for treating infections from hepatitis delta and related viruses which comprises administering to a mammal in need thereof a therapeutically effective amount of a compound of claim 1.

26. A method for preventing restenosis which comprises administering to a mammal in need thereof a therapeutically effective amount of a compound of claim 1.

27. A method for treating polycystic kidney disease which comprises administering to a mammal in need thereof a therapeutically effective amount of a compound of claim 1.

28. A method for treating or preventing a disease selected from cancer, neurofibromin benign proliferative disorder, blindness related to retinal vascularization, infections from hepatitis delta and related viruses, restenosis and polycystic kidney disease, which comprises administering to a mammal in need thereof a therapeutically effective amount of a compound of claim 1.

* * * * *